(12) United States Patent
Goyal

(10) Patent No.: US 10,182,878 B2
(45) Date of Patent: Jan. 22, 2019

(54) SYSTEMS AND METHODS FOR ENHANCING PREPARATION AND COMPLETION OF SURGICAL AND MEDICAL PROCEDURES

(71) Applicant: MG STROKE ANALYTICS INC., Calgary, CA (US)

(72) Inventor: Mayank Goyal, Calgary (CA)

(73) Assignee: MG STROKE ANALYTICS INC., Calgary (CA)

(*) Notice: Subject to any disclaimer, the term of this patent is extended or adjusted under 35 U.S.C. 154(b) by 0 days.

(21) Appl. No.: 15/634,001

(22) Filed: Jun. 27, 2017

(65) Prior Publication Data

US 2017/0290636 A1 Oct. 12, 2017

Related U.S. Application Data

(63) Continuation of application No. 14/870,705, filed on Sep. 30, 2015, now Pat. No. 9,717,562, which is a (Continued)

(51) Int. Cl.
*A61B 50/33* (2016.01)
*A61B 17/22* (2006.01)
(Continued)

(52) U.S. Cl.
CPC ............ *A61B 50/33* (2016.02); *A61B 17/22* (2013.01); *A61B 17/28* (2013.01);
(Continued)

(58) Field of Classification Search
CPC ..... A61B 17/22; A61B 17/32; A61B 17/3215; A61B 18/14; A61B 19/02; A61B 19/026; A61B 19/0271; A61B 19/08; A61B 46/00; A61B 50/33; A61B 2017/22001; A61B 2017/320741; A61B 2019/0202; A61B 2019/0277; A61B 2019/0278; A61B 2050/3008; A61B 17/28; A61B 50/30; A61F 2/82; A61M 5/178; A61M 19/00;
(Continued)

(56) References Cited

U.S. PATENT DOCUMENTS 3,802,555 A * 4/1974 Grasty ................... A61B 50/30
206/370
4,226,328 A * 10/1980 Beddow .................. A61F 17/00
206/364

(Continued)

*Primary Examiner* — Bryon Gehman
(74) *Attorney, Agent, or Firm* — McGlew and Tuttle, P.C.

(57) ABSTRACT

Systems and methods for preparing and completing surgical and medical procedures. In particular, kits are provided for improving preparation and completion time for a medical or surgical procedure in which the kit includes modularized compartments containing sterilized medical or surgical equipment and wherein the medical or surgical equipment is organized and/or ordered within the kit to generally correspond to the sequence of steps of the medical or surgical procedure. The kit is particularly applicable to recanalization procedures for stroke patients as well as revascularization procedures for acute myocardial infarction patients where a kit enables faster preparation and completion of these procedures.

20 Claims, 14 Drawing Sheets

Related U.S. Application Data continuation of application No. 14/005,167, filed as application No. PCT/CA2013/000533 on Jun. 3, 2013, now Pat. No. 9,186,217.

(60) Provisional application No. 61/655,854, filed on Jun. 5, 2012.

(51) Int. Cl.

| *A61F 2/82* | (2013.01) |
| *A61M 25/00* | (2006.01) |
| *A61B 46/00* | (2016.01) |
| *A61B 17/28* | (2006.01) |
| *A61B 17/3215* | (2006.01) |
| *A61M 5/178* | (2006.01) |
| *A61M 19/00* | (2006.01) |
| *A61M 25/06* | (2006.01) |
| *A61M 25/09* | (2006.01) |
| *A61M 39/06* | (2006.01) |
| *A61B 50/30* | (2016.01) |
| *A61B 50/00* | (2016.01) |
| *A61M 39/22* | (2006.01) |

(52) U.S. Cl.
CPC .......... *A61B 17/3215* (2013.01); *A61B 46/00* (2016.02); *A61B 50/30* (2016.02); *A61F 2/82* (2013.01); *A61M 5/178* (2013.01); *A61M 19/00* (2013.01); *A61M 25/002* (2013.01); *A61M 25/065* (2013.01); *A61M 25/09* (2013.01); *A61M 39/06* (2013.01); *A61B 2017/22001* (2013.01); *A61B 2017/22051* (2013.01); *A61B 2050/005* (2016.02); *A61B 2050/3007* (2016.02); *A61B 2050/3008* (2016.02); *A61M 2039/062* (2013.01); *A61M 2039/229* (2013.01); *A61M 2209/06* (2013.01)

(58) Field of Classification Search
CPC .. A61M 25/002; A61M 25/065; A61M 25/09; A61M 39/06
USPC .............. 206/363–370, 438, 570–572; 600/562–567; 604/28, 35; 606/1, 159, 606/167–185
See application file for complete search history.

(56) References Cited

U.S. PATENT DOCUMENTS

| | | | | |
|---|---|---|---|---|
| 4,447,236 A | * | 5/1984 | Quinn | A61M 39/223 604/164.09 |
| 4,501,363 A | * | 2/1985 | Isbey, Jr. | A61B 50/33 206/363 |
| 4,523,679 A | * | 6/1985 | Paikoff | A61L 2/04 206/363 |
| 4,936,448 A | * | 6/1990 | Holloway | A61M 25/002 206/364 |
| 5,144,942 A | * | 9/1992 | Decarie | A61B 1/00144 206/363 |
| 5,868,250 A | * | 2/1999 | Brackett | A61M 5/008 206/363 |
| 6,187,768 B1 | * | 2/2001 | Welle | A61L 2/18 514/152 |
| 6,417,639 B1 | * | 7/2002 | Schillaci | G11B 5/5526 318/254.1 |
| 6,588,587 B2 | * | 7/2003 | Johnson | B25H 3/021 206/363 |
| 6,692,462 B2 | * | 2/2004 | Mackenzie | A61B 17/3415 604/104 |
| 6,896,141 B2 | * | 5/2005 | McMichael | A61B 50/30 206/370 |
| 6,907,992 B2 | * | 6/2005 | McMichael | A61B 50/30 206/370 |
| 7,100,771 B2 | * | 9/2006 | Massengale | A61M 5/002 206/363 |
| 7,141,045 B2 | * | 11/2006 | Johansson | A61B 5/14539 604/508 |
| 7,288,099 B2 | * | 10/2007 | Deem | A61B 17/064 606/151 |
| 7,323,006 B2 | * | 1/2008 | Andreas | A61F 2/958 600/585 |
| 7,331,462 B2 | * | 2/2008 | Steppe | A61B 50/30 206/370 |
| 7,401,703 B2 | * | 7/2008 | McMichael | A61B 50/33 206/370 |
| 7,434,687 B2 | * | 10/2008 | Itou | A61M 25/002 206/363 |
| 7,491,176 B2 | * | 2/2009 | Mann | A61B 10/0096 206/363 |
| 8,088,140 B2 | * | 1/2012 | Ferrera | A61B 17/221 606/113 |
| 8,177,064 B2 | * | 5/2012 | McCormick | A61B 50/33 206/370 |
| 8,240,468 B2 | * | 8/2012 | Wilkinson | A61B 5/417 206/363 |
| 8,323,271 B2 | * | 12/2012 | Humayun | A61F 9/00736 606/1 |
| 8,568,391 B2 | * | 10/2013 | Kerns | A61B 50/33 606/1 |
| 8,685,068 B2 | * | 4/2014 | Sixto | A61B 17/8014 606/286 |
| 8,701,890 B2 | * | 4/2014 | Bertazzoni | A61B 17/154 206/572 |
| 8,979,829 B2 | * | 3/2015 | Tomasello | A61B 18/24 606/10 |
| 9,211,596 B2 | * | 12/2015 | Hecht | B23C 5/22 |
| 2002/0185406 A1 | * | 12/2002 | Massengale | A61M 5/002 206/571 |
| 2007/0142786 A1 | * | 6/2007 | Lampropoulos | A61M 5/008 604/189 |
| 2008/0125634 A1 | * | 5/2008 | Ryan | A61B 5/01 600/342 |
| 2010/0274205 A1 | * | 10/2010 | Morelli | A61M 1/0088 604/290 |

* cited by examiner

MULTI-LAYER CONFIGURATION 1

MULTI-LAYER HYBRID CONFIGURATION

SINGLE LAYER CONFIGURATION

MULTI-LAYER CONFIGURATION 2

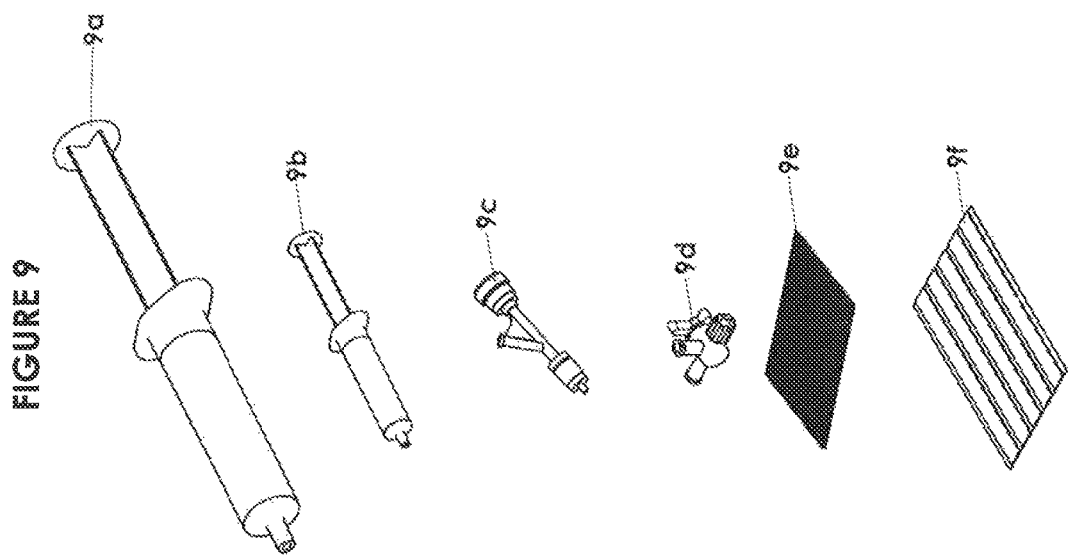

SYSTEMS AND METHODS FOR ENHANCING PREPARATION AND COMPLETION OF SURGICAL AND MEDICAL PROCEDURES

CROSS REFERENCE TO RELATED APPLICATIONS

This application is a continuation under 37 CFR 1.53(b) of prior U.S. patent application Ser. No. 14/870,705 filed Sep. 30, 2015 and claims the benefit of U.S. patent application Ser. No. 14/005,167 filed Sep. 13, 2013, which is now U.S. Pat. No. 9,186,217, and claims the benefit (35 U.S.C. § 120 and 365(c)) of International Application PCT/CA2013/000533 filed Jun. 3, 2013, which designated inter alia the United States and which claims the priority of U.S. Provisional Patent Application 61/655,854 filed Jun. 5, 2012, the entire contents of each application are incorporated herein by reference.

FIELD OF THE INVENTION

The present invention relates to systems and methods for preparing and completing surgical and medical procedures. In particular, the invention relates to kits for improving preparation and completion time for a medical or surgical procedure in which the kit includes modularized compartments containing sterilized medical or surgical equipment and wherein the medical or surgical equipment is organized and/or ordered within the kit to generally correspond to the sequence of steps of the medical or surgical procedure. The kit is particularly applicable to recanalization procedures for stroke patients as well as revascularization procedures for acute myocardial infarction patients where a kit enables faster preparation and completion of these procedures.

BACKGROUND OF THE INVENTION

Many surgical and medical procedures are sophisticated and/or complex procedures that require substantial and coordinated contributions from a number of different medical practitioners including physicians, nurses, technologists and other assistants.

In particular, many procedures require that teams of medical practitioners work together through an orchestrated sequence of steps to ensure that best practices for the delivery of a particular procedure is attained in accordance with a particular standard of patient care. For example, most surgical and medical procedures follow a logical sequence of steps that may involve any combination of assessment, diagnosis, imaging, preparation, procedure and follow-up.

Importantly, in many scenarios, while best practices may suggest that preferred procedures be followed, the particulars of an emergency medical condition may limit the ability of the medical team to complete the preferred steps either because of time constraints and/or the availability of equipment and/or tools to enable those steps.

For example, in the case of assessing and treating stroke patients suffering from cerebral arterial blockage, time to recanalization of cerebral arteries is a critical factor in patient outcome where the extent of brain damage may be significantly affected by the time taken to effect recanalization.

That is, any time saved during the procedures to assess, diagnose, image and treat a stroke patient may have significant effects on the status of the patient. While different steps in the process continue to be improved, for example, imaging and recanalization technologies continue to improve, other steps within the overall assessment and treatment protocols can be inefficient.

More specifically, the ability to achieve intra-arterial (IA) recanalization keeps getting better as demonstrated by studies (such as SWIFT, TREVO and others) and based on availability of newer devices such as Solitaire™, Penumbra™, or Trevo™. In most acute ischemic stroke patients, core (tissue which is already dead) expands into penumbra (tissue at risk of dying if reperfusion is not achieved emergently) over a period of time. While the ability to measure core is quite good, it is not perfect and the ability to measure how fast core is growing generally cannot be readily quantified. As such, it remains important to achieve recanalization as quickly as possible.

In a typical scenario, a patient having a stroke will go through the following sequence of steps. These will typically include recognizing symptoms, calling 911, and getting to the hospital and importantly the correct hospital. At the hospital, the patient will undergo clinical evaluation followed by imaging which will determine if the stroke is ischemic or hemorrhagic. If the stroke is ischemic, further imaging such as CTA (computer tomography angiography), CTP (computer tomography perfusion) and/or MRI (magnetic resonance imaging) may be undertaken. If there is large vessel proximal occlusion, a decision based on a number of factors will determine if the patient goes to a catheter lab (Cath-Lab) to attempt intra-arterial recanalization. Generally speaking Cath-Lab procedures are done for bad, potentially disabling strokes.

When the decision is made to initiate surgical treatment, a number of factors will come into play that must all be managed to enable treatment in what is a complex emergency situation. These factors include the time of day (may be after regular staffing hours), the assembly of different teams and the requirements for patient monitoring, anesthesia, consent and patient preparation for the procedure.

Due to the number of people involved as well as the surgical equipment involved, the setting up for the procedure is often confusing and time consuming. For example, there are at least 50 pieces of separate equipment that need to be opened from individual packets in order for a typical recanalization procedure to be initiated and each packet must be opened and/or prepared in a particular order. Catheters and other lines need to be flushed and attached to a pressure line in such a way that no air remains in the lines.

Further still, particularly when such procedures are being conducted as an emergency outside normal staffing hours, different members of the team may reach the lab at slightly different times. Depending on the time of arrival and the particular training of the team members, it may be difficult for certain team members to initiate the preparatory steps due to the lack of training to assemble and/or undertake such steps. Any delays in preparing the patient and/or the equipment will result in delays in initiating and completing the medical procedure itself. Moreover, medical teams do not want to be assembling or looking for equipment in the middle of the night when the procedure may be required. In addition, it may be desired that the procedure is performed at a hospital or treatment facility where the procedure is not routinely performed with the result being that a physician/medical team may not be familiar with the layout of an operating room and/or the storage locations of the equipment. As such, there is a need for equipment to be transportable in a convenient form so as to minimize time delays under these conditions.

In other words, there can be significant delays in the time from patient diagnosis to the commencement and completion of a recanalization procedure due to the time required to organize and deploy the surgical equipment.

Similarly, the same issues apply to the diagnosis and treatment of acute myocardial infarction patients. As with stroke patients, time is a critical factor in diagnosing and treating such patients. Also, the patient preparation and treatment procedures for recanalization and revascularization procedures are substantially similar in certain respects. That is, in undertaking treatment procedures in both acute stroke and myocardial infarction patients, catheter procedures are utilized to gain access to affected vessels and to effect treatment of those vessels by clot removal or coronary artery opening by balloon angioplasty and/or stenting.

A review of the prior art indicates that various surgical kits have been the subject of patent protection. However, the prior art does consider and does not teach or suggest a solution to the technical problem of more efficiently preparing for and undertaking an recanalization and revascularization procedures.

Examples of past surgical kits are discussed briefly below.

U.S. Pat. No. 7,288,090 describes an electrophysiological procedure kit containing the internal indifferent electrode device, a surgical probe and other tools or devices that may be required for a procedure.

U.S. Patent Application Publication No. 2011/0071572 describes a sterile single-use disposable orthopedic surgery kit for the internal fixation of fractured bones. The kit includes a single bone plate precontoured and sized to match the patient's anatomic shape. The kit includes a briefcase-like container that has partitions for compartmentalization, with all the components visible and accessible when the container is open.

U.S. Pat. No. 7,331,462 describes a kit management system for use in microsurgery that includes a plurality of tubing, surgical instruments, connectors, an instrument tray, a connector tray, and a tubing organizer. The tubing organizer secures and separates the tubing in a spaced relationship as needed during microsurgery.

U.S. Patent Application Publication No. 2003/0159969 and U.S. Pat. No. 7,401,703 describe a surgical kit including a tray having a plurality of planar surfaces with recesses for holding surgical implements. The planar surfaces are vertically offset from one another such that items in the top surface must be removed before items below can be accessed.

U.S. Pat. No. 4,501,363 describes a surgical kit having a pair of trays wherein one tray is received inside the other. Each tray includes a plurality of embossments in its bottom for receiving various surgical supplies. After the completion of the surgery, the inner tray is flipped over and set on top the outer tray to form a receptacle for post-operative materials.

U.S. Patent Application Publication No. 2011/0186456 describes a system of surgical instruments for knee surgery having various containers. Size-specific instruments are grouped in the containers according to size, such that once it is determined that a certain size of instruments are needed for a specific surgery, only the container(s) containing the necessary size of instruments needs to be opened.

U.S. Pat. No. 5,868,250 describes a tray for dispensing and receiving surgical equipment. The tray includes a bar for holding surgical instruments, particularly sharp instruments, that pivots upwardly into a raised position to allow the instruments to be easily removed from and returned to the bar. The bar may also be hollow to allow antiseptic solution to be pumped through it for sterilizing the instruments.

U.S. Patent Application Publication No. 2010/0274205 describes a wound treatment kit comprising three containers divided by the order of steps for treating a wound, specifically 1) preparation; 2) dressing; and 3) sealing.

U.S. Patent Application Publication No. 2002/0185406 and U.S. Pat. No. 7,100,771 describe a sterile pain management kit containing the primary medical supplies needed for performing a continuous nerve block procedure.

U.S. Pat. No. 8,240,468 describes a pre-packaged medical device including a tray for supporting the medical device, such as a blood collection set including a needle assembly and a tube holder.

U.S. Pat. No. 6,588,587 describes a packaging system for medical devices and surgical components used in heart by-pass surgery.

U.S. Pat. No. 6,412,639 describes a medical procedure kit containing surgical tools and medical adhesive. The medical adhesive may be independently sterilized and wrapped from the other surgical tools in the kit.

U.S. Pat. No. 4,523,679 describes a pre-sterilized medical procedure kit that contains a first unit pre-sterilized by ethylene oxide and a second unit containing a heat sterilized vial of medicament agent that is incompatible with ethylene oxide sterilization.

In view of the foregoing, there continues to be a need for systems and methodologies that address the foregoing problems with regards to IA recanalization and revascularization procedures and that specifically enable a medical team to reduce the total time that may be required to complete these procedures. In particular, there has been a need for systems and methodologies that permit members of a medical team to initiate the preparatory steps of a complex recanalization or revascularization procedure without requiring the assembly of the complete medical team. More specifically, there has been a need for modularized bundles of groups of recanalization or revascularization surgical equipment that enables different members of a surgical team to quickly and efficiently have access to equipment used in these procedures and where the layout of the modularized bundles logically corresponds to steps of the procedure.

SUMMARY OF THE INVENTION

In accordance with the invention, there is provided systems and methodologies to initiate the preparatory steps of a complex medical or surgical procedure and particularly recanalization and revascularization procedures without requiring the assembly of the complete medical team.

In accordance with a first embodiment, there is provided a modular kit for decreasing preparation and surgical time for a recanalization or revascularization procedure in the treatment of acute stroke and acute myocardial patients comprising: at least one tray having a plurality of compartments containing a plurality of equipment modules containing sterilized surgical equipment to conduct individual steps of the procedure, the individual steps including surgical site preparation, tube and catheter flushing, and arterial access steps of the procedure. In one embodiment, the equipment modules include a surgical site preparation module, a tube and catheter flushing module and an arterial access module. Such equipment can include tube and catheter equipment to conduct a recanalization or revascularization procedure.

In one embodiment, the kit includes outer packaging providing a sterile seal to the at least one tray and the equipment modules. The at least one tray may include a lower tray stackable with an upper tray with the upper tray including surgical site preparation equipment or the lower tray may include the surgical site preparation equipment. The kit may also be a single tray or a combination of stacked and unstacked trays.

In one embodiment, the tube and catheter flushing module includes at least one catheter flushing manifold, the catheter flushing manifold including a first port for operative connection to a flushing system and at least two catheter openings for connection to catheters and wherein activation of the flushing system enables simultaneous flushing of each connected catheter. In one embodiment, the at least two catheter openings will have different diameters.

In one embodiment, the kit includes a bowl compartment integrally formed with the at least one tray. The bowl compartment may support a separable bowl. In one embodiment, the bowl compartment includes a sterile seal on an upper surface of the at least one tray and the bowl compartment supports liquid within the tray.

In one embodiment, each of the surgical site preparation module, tube and catheter flushing module and arterial access module are separate trays separable from one another.

In preferred embodiments, the surgical site preparation module includes cleaning and draping equipment and the tube and catheter flushing module includes catheter flushing equipment.

In one embodiment, the procedure module includes intra-arterial recanalization equipment, the intra-arterial recanalization equipment including a plurality of catheters for accessing neck and brain vessels and clot retrieval. In another embodiment, the procedure module includes an acute myocardial infarction (MI) equipment module, the acute MI equipment including a plurality of catheters for accessing neck and coronary arterial vessels and a plurality of microcatheters, microwires, angioplasty balloons and stents for dilating of stenosed coronary vessels.

In yet another embodiment, each catheter within the procedure module includes a pre-attached rotating hemostatic valve (RHVs) or three-way stop-cock.

In a further embodiment, the procedure module includes at least two clot retrieval devices individually sealed within the procedure module to enable collection and re-use of equipment unused in the procedure. The kit may also include an equipment return module having labelling and packaging for packaging unused equipment for return to a manufacturer.

In one embodiment, the surgical equipment in the each of the surgical site preparation module, the tube and catheter flushing module and arterial access module include module packaging only and are not individually packaged.

In another aspect, the invention provides a method for decreasing preparation and surgical time for a recanalization or revascularization procedure in the treatment of acute stroke and acute myocardial infarction patients comprising the steps of: a. accessing a modular kit having at least one tray having a plurality of compartments containing a plurality of equipment modules containing sterilized surgical equipment to conduct individual steps of the recanalization or revascularization procedure, the compartments containing surgical site preparation equipment, tube and catheter flushing equipment, arterial access equipment and recanalization or revascularization equipment; b. preparing the surgical site using the surgical site preparation equipment; and, c. conducting tube and catheter flushing of the recanalization or revascularization equipment.

In another embodiment, step c. includes conducting simultaneous flushing of at least two tubes or catheters of the recanalization or revascularization equipment.

In yet another embodiment, the method further comprises the step of providing an equipment return module within the kit having labelling or packaging and returning unused procedure equipment to a manufacturer using the labelling or packaging.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is an isometric view of typical miscellaneous equipment for inclusion in a module of a recanalization kit in accordance with one embodiment of the invention;

DESCRIPTION OF THE PREFERRED EMBODIMENTS

With reference to the figures, systems and methodologies to initiate the preparation for and completion of intra-arterial (IA) recanalization and revascularization procedures for acute ischemic stroke and acute myocardial infarction patients are described. For the purposes of description, the invention is described with primary reference to IA recanalization or revascularization procedures. As discussed within this description, it is understood that the invention can be applied to other procedures.

The system generally provides a multi-compartment, modularized kit containing the required equipment to prepare a patient for an IA recanalization procedure and to undertake the procedure wherein the equipment is ordered within the modularized kit to generally correspond to the sequence of steps of an IA recanalization procedure. That is, and in accordance with an IA recanalization procedure, the equipment is generally ordered to enable surgical site preparation, tube and catheter flushing, arterial access and procedure completion. Importantly, it is understood that the specific medical or surgical equipment within the modularized kit may be varied in accordance with changes in the medical or surgical equipment that may be utilized for such a procedure and any reference in this application to specific medical equipment (for example, as listed in Appendix A) is for illustrative purposes only and that workers skilled in the art may substitute alternate equipment without departing from the scope of the invention as defined by the claims.

In the context of this description, the term "modular" or an "equipment module" generally means the organization of functional groups of medical equipment that may be used for a particular step or series of steps within an overall medical procedure. However, the term modular or equipment module does not necessarily mean a specific compartment or spatially separated area within a larger collection or organization of equipment used for the overall medical procedure. That is, a single module of equipment may be located in one compartment and comprise several pieces of equipment. A single module of equipment may also be located in more than one compartment and comprise one or more pieces of equipment in each compartment. A single module of equipment may include more than one compartment that are physically separable from one another or be integral with one another.

Figure 1:
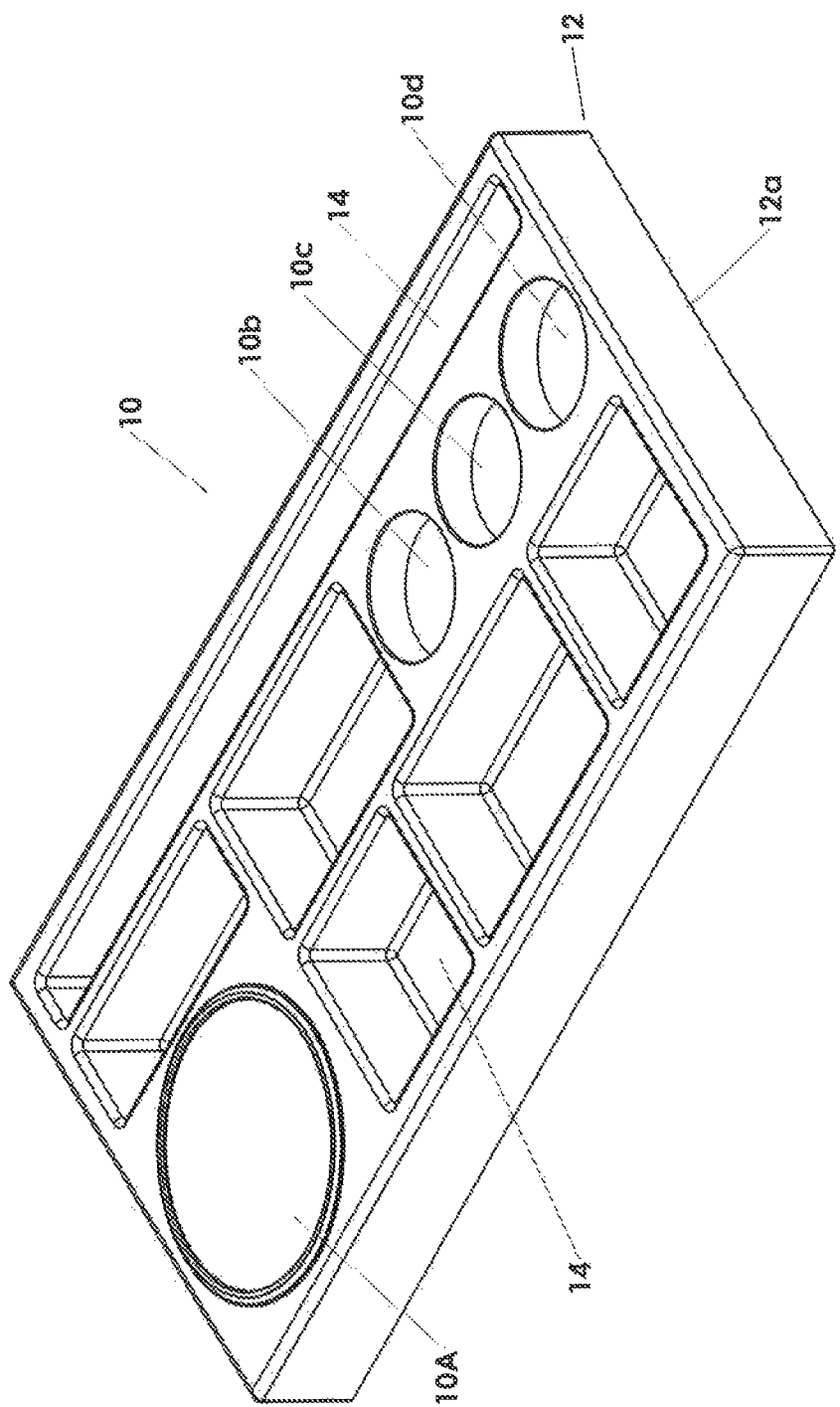
FIG. 1 is an isometric view of a modularized equipment tray of an intra-arterial (IA) recanalization kit in accordance with one embodiment of the invention.
Figure 1B:
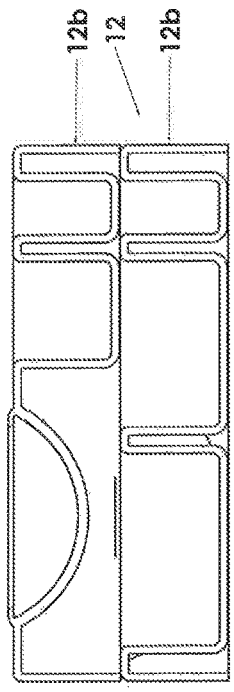
FIG. 1B is an end view of a two-layer modularized equipment tray of an intra-arterial (IA) recanalization kit in accordance with one embodiment of the invention.
Figure 1D:
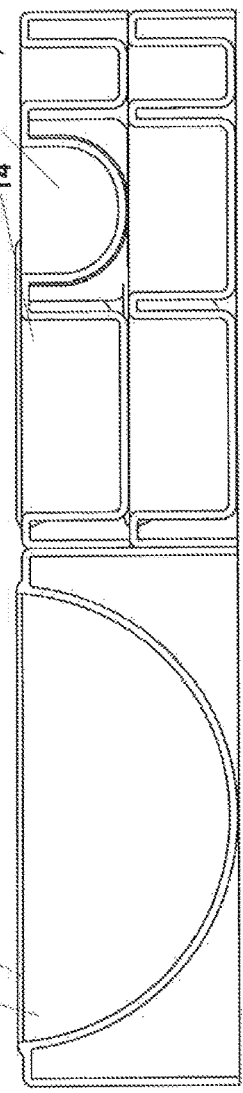
FIG. 1D is an end view of a hybrid modularized equipment tray of an intra-arterial (IA) recanalization kit in accordance with one embodiment of the invention.
Figure 1A:
FIG. 1A is an end view of a modularized equipment tray of an intra-arterial (IA) recanalization kit in accordance with one embodiment of the invention.
Figure 1C:
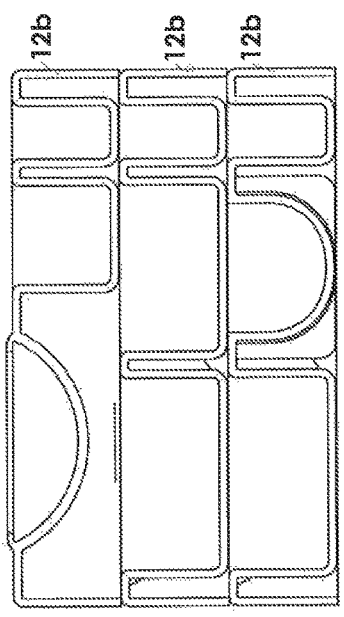
FIG. 1C is an end view of a three-layer modularized equipment tray of an intra-arterial (IA) recanalization kit in accordance with one embodiment of the invention.

As shown in the Figures, the kit 10 includes one or more trays 12 having compartmentalized sections 14 for containing medical equipment for a) preparing a patient for an IA recanalization procedure and b) undertaking the procedure. FIGS. 1 and 1A show an embodiment of the kit with a single unstacked tray 12a, FIG. 1B shows a stacked tray 12b embodiment with two layers, FIG. 1C shows a stacked tray 12b embodiment having three layers and FIG. 1D shows a hybrid embodiment showing a combination of two stacked 12b and unstacked 12a trays. Generally, in the context of the description, a tray is a supporting base structure used to support and/or contain the kit modules.

Regardless of the embodiment, each tray includes at least one compartment 14 for containing specific equipment for preparing a patient for and performing IA recanalization. The trays and/or compartments are laid out in a logical order that generally corresponds to the sequence of steps of preparing for and undertaking an IA recanalization procedure. In one embodiment, containing multiple trays, the trays may be physically separated for distribution to different locations in an operating room to enable different members of the team to have access to the specific equipment they require.

Figure 12:
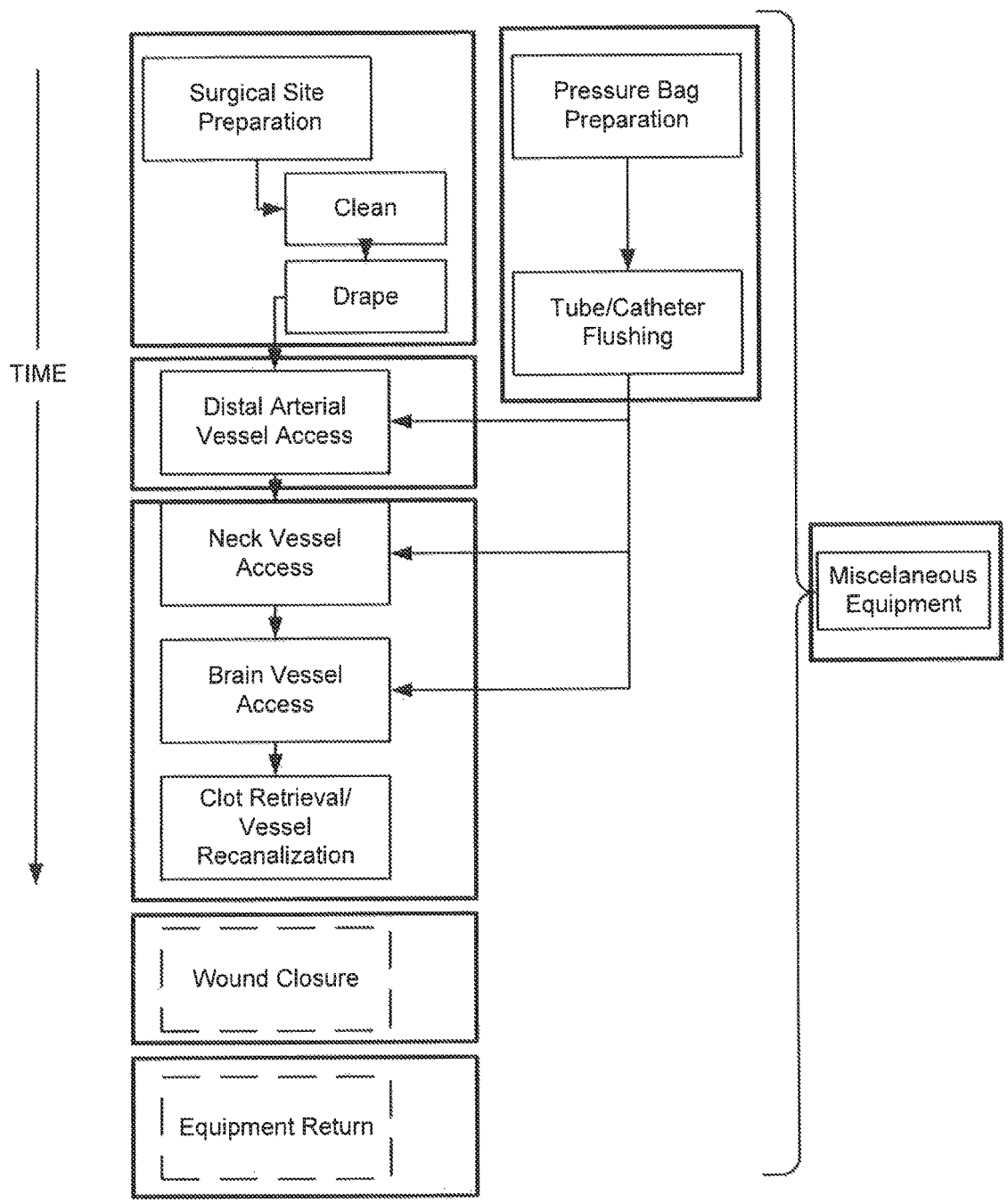
FIG. 12 is a view of a conceptual time layout of the key steps of an IA recanalization procedure.

FIGS. 2-10 show various groups of equipment that may be packaged as modules to enable each of the preparation and surgical steps to be completed. FIG. 12 is an overview of the time sequence of the preparation and surgical steps. In the context of this description, as noted above, a module may include one or more pieces of surgical equipment. In one embodiment, each piece of surgical equipment may be individually packaged in a sterile package and may be collectively packaged within outer packaging. Each module of equipment is located within a tray in one or more compartments 14. If equipment of one module is located in more than one compartment, the compartments are preferably adjacent one another and/or part of a common tray. In one embodiment, modules of equipment are individual packaged and in one embodiment as described in greater detail below, valuable pieces of pieces are individually packaged so as to enable their return to a manufacturer in the event that they are not used during the procedure.

Figure 2:
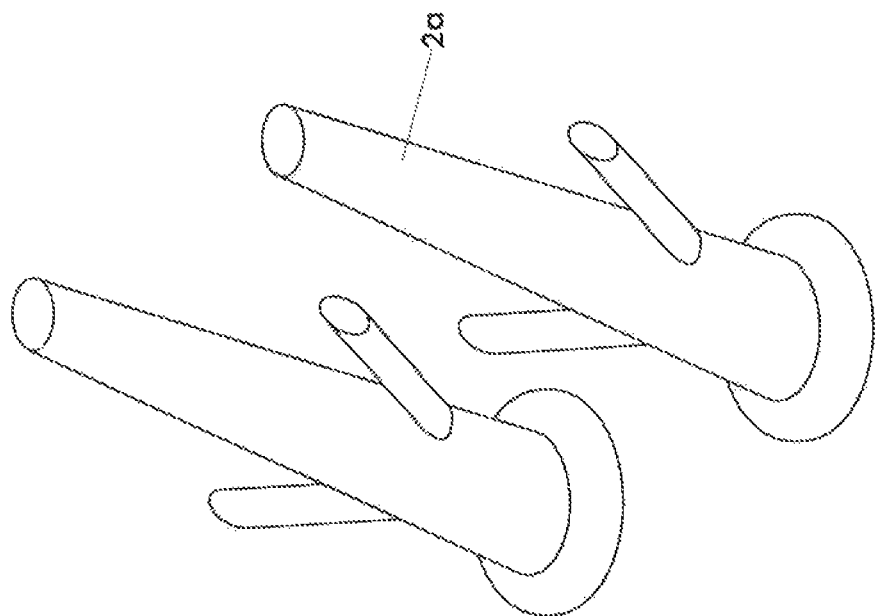
FIG. 2 is an isometric view of typical surgical site scrubbing equipment for inclusion in a module of a recanalization kit in accordance with one embodiment of the invention.

FIG. 2 shows surgical site cleaning equipment that may be included in a first module. The first module may include cleaning equipment such as skin cleaning equipment 2a and a disposable electric razor (not shown).

Figure 3:
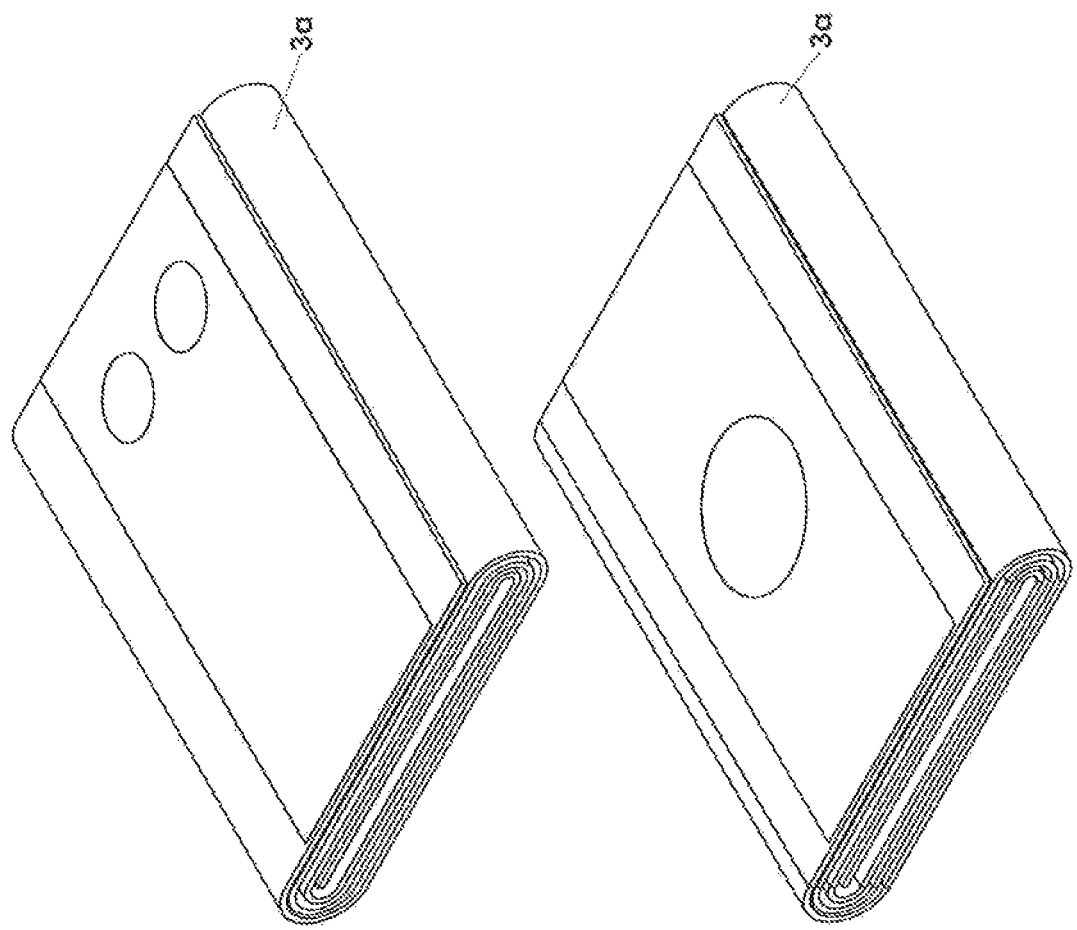
FIG. 3 is an isometric view of typical surgical drapes for inclusion in a module of a recanalization kit in accordance with one embodiment of the invention.

FIG. 3 shows typical surgical drapes 3a that are applied over the surgical site and that may be included in the first module or a separate module.

Figure 4:
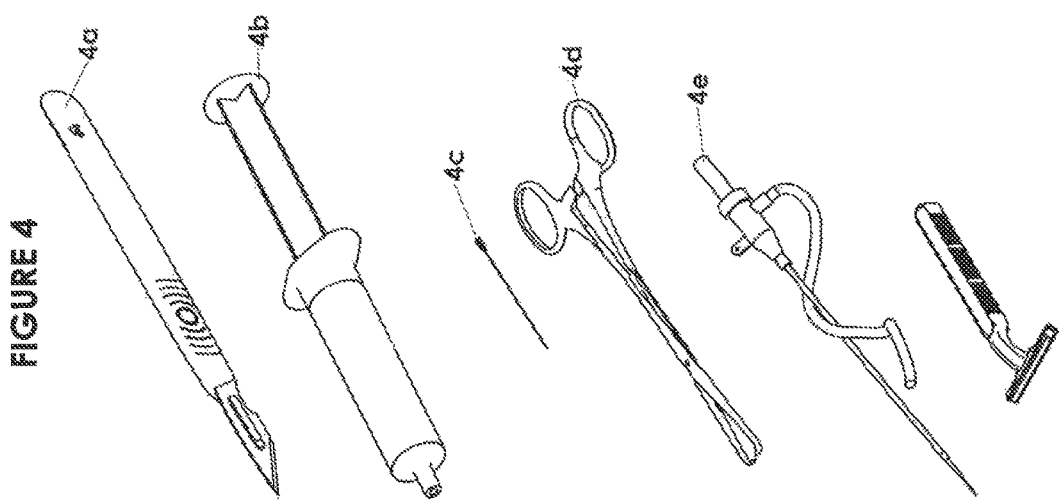
FIG. 4 is an isometric view of typical arterial access equipment for inclusion in a module of a recanalization kit in accordance with one embodiment of the invention.

FIG. 4 shows arterial access equipment and may include a scalpel 4a, syringe preloaded or along with local anesthetic 4b, puncture needle 4c, forceps 4d and small introducer wire 4e. The arterial access equipment is preferably contained in a distinct module.

Figure 5:
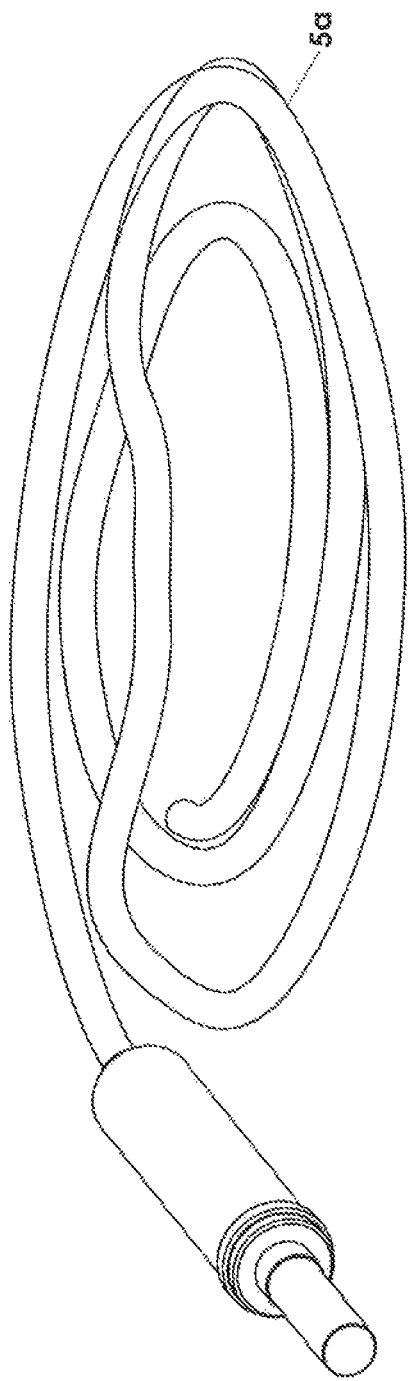
FIG. 5 is an isometric view of typical pressure bag connecting tubes for inclusion in a module of a recanalization kit in accordance with one embodiment of the invention.

FIG. 5 shows typical connecting tubes 5a for pressure bags (not shown) that enable connection of pressure bags to tube flushing equipment.

Figure 6:
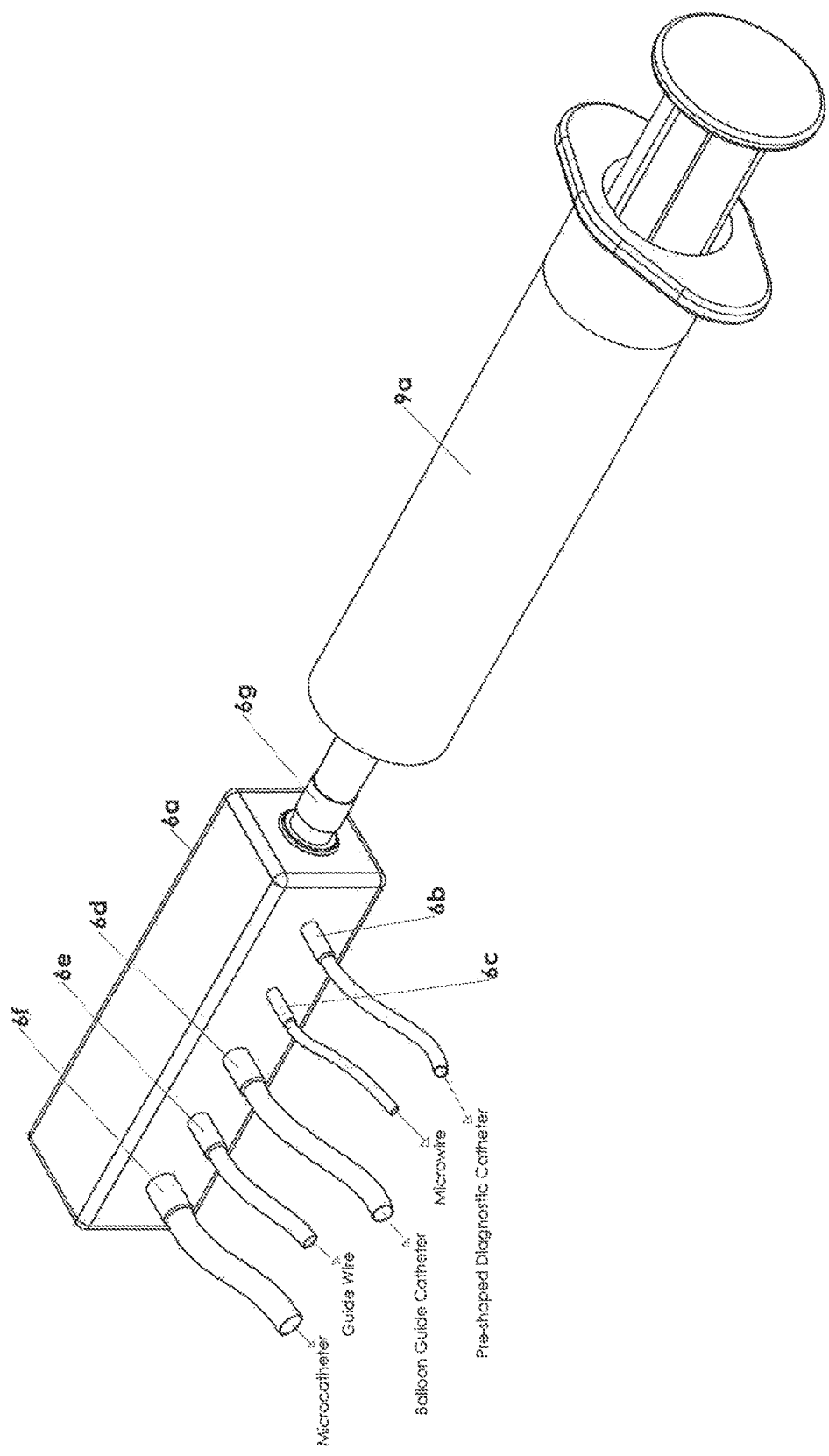
FIG. 6 is an isometric view of a flushing manifold for inclusion in a module of a recanalization kit in accordance with one embodiment of the invention.

FIG. 6 shows a manifold 5a that enables simultaneous flushing of multiple tubes of different diameters. The manifold is described in greater detail below. The connecting tubes and manifolds may be contained in a single or separate module.

Figure 7:
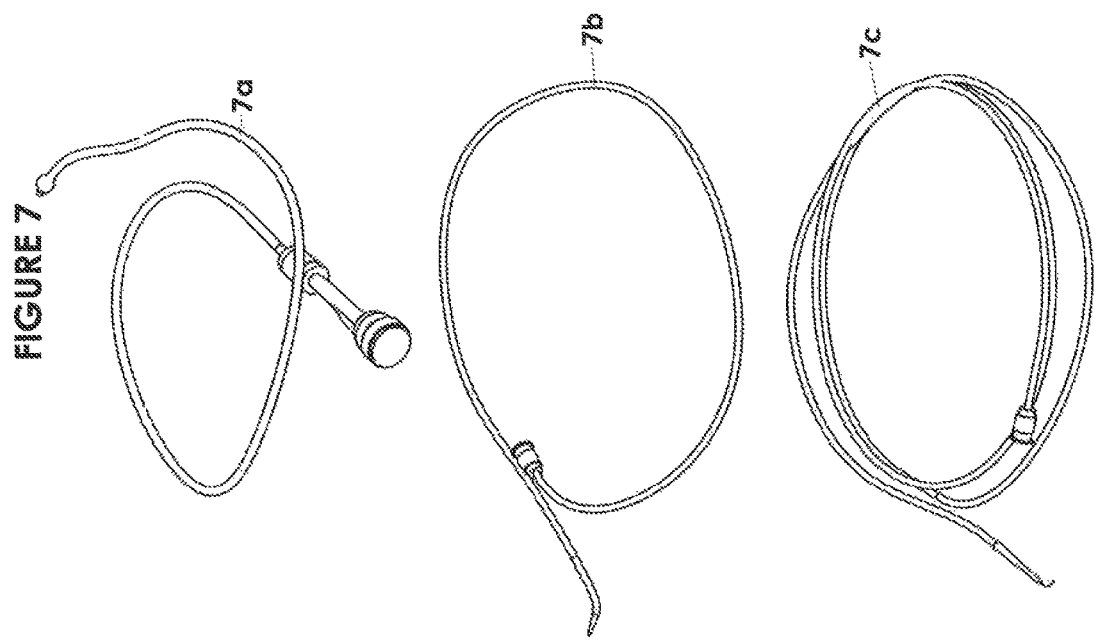
FIG. 7 is an isometric view of typical neck vessel access equipment for inclusion in a module of a recanalization kit in accordance with one embodiment of the invention.

FIG. 7 shows neck vessel access equipment and may typically include a balloon guide catheter 7a, one or more pre-shaped diagnostic catheter(s) 7b and guide wire 7c. Each of the balloon guide catheter 7a, pre-shaped diagnostic catheter 7b and guide wire 7c are preferably contained within a single module. These would vary in size and shape if it were being designed for coronary access.

Figure 8:
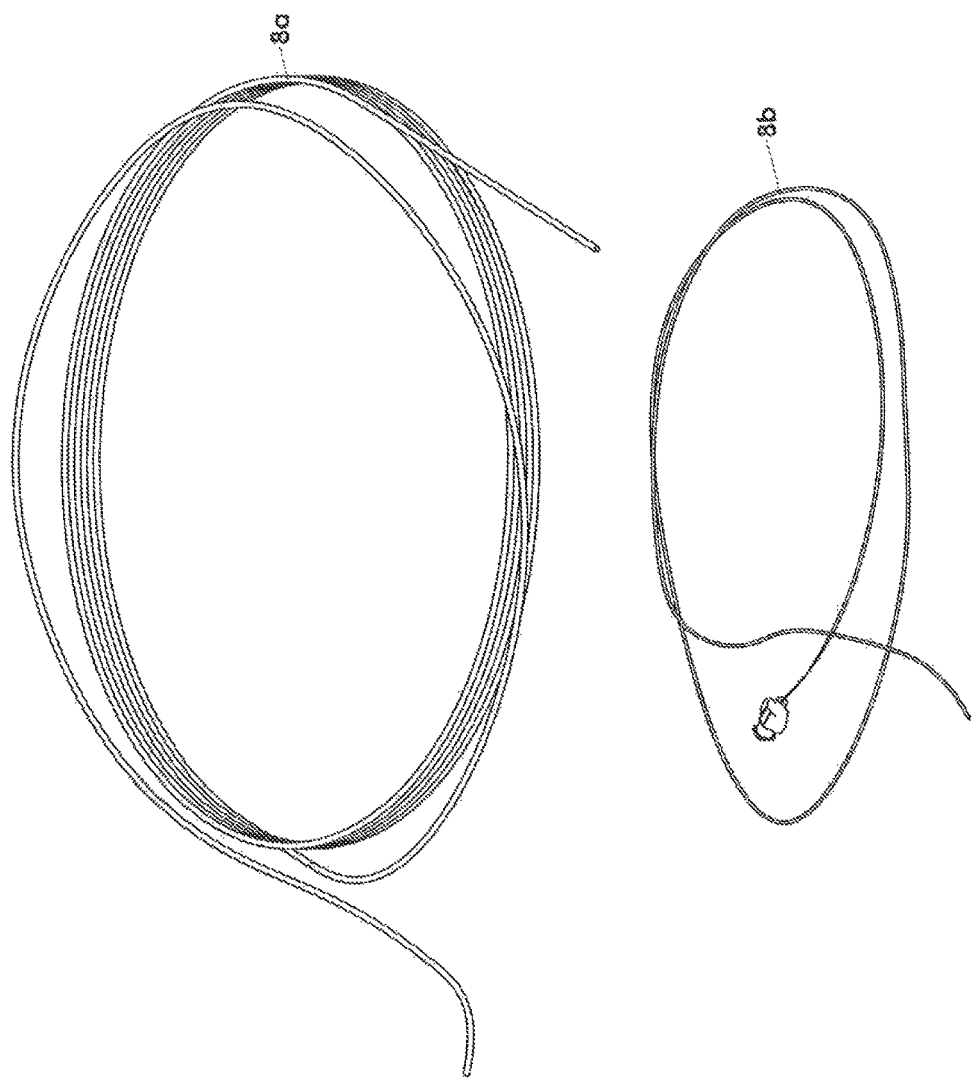
FIG. 8 is an isometric view of typical brain vessel access equipment for inclusion in a module of a recanalization kit in accordance with one embodiment of the invention.
Figure 8A:
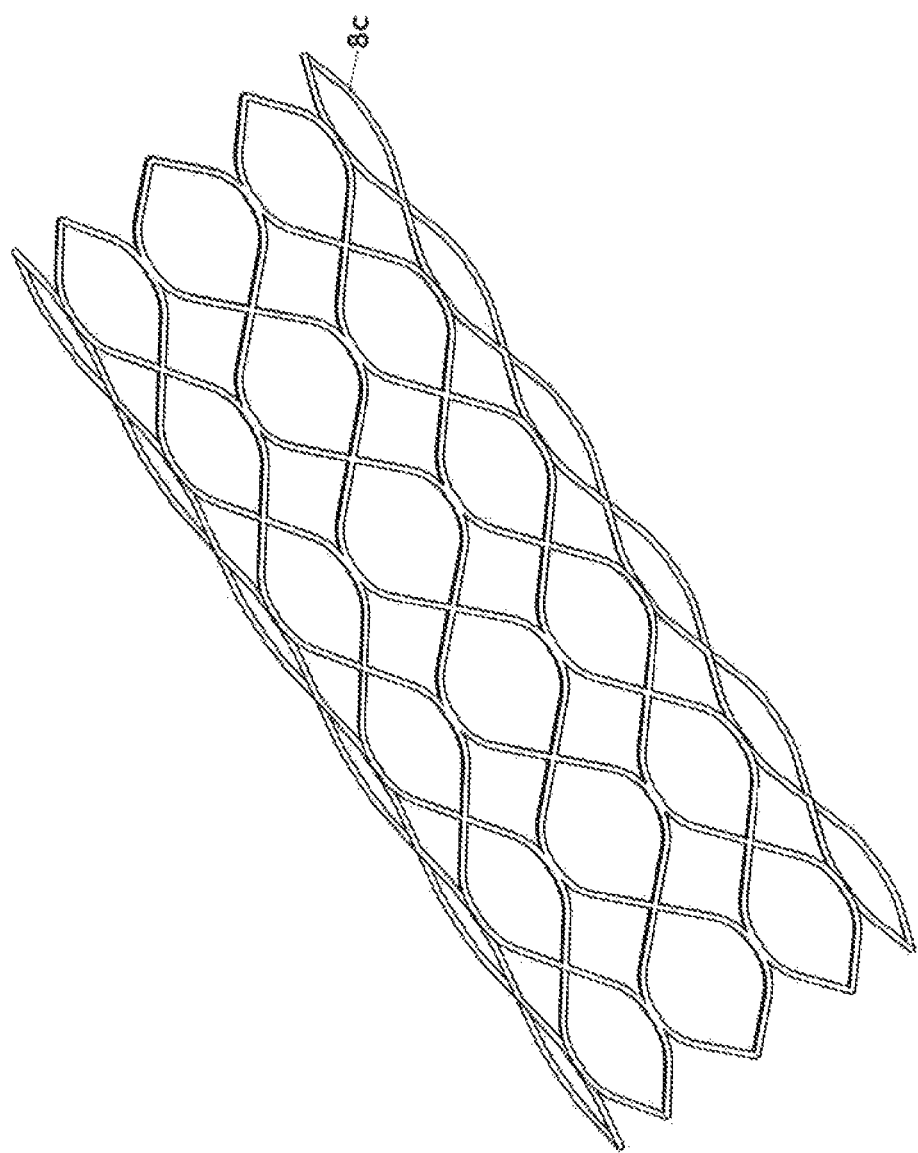
FIG. 8A is an isometric view of a typical clot retrieval device for inclusion in a module of a recanalization kit in accordance with one embodiment of the invention.

FIGS. 8 and 8A shows brain vessel access and clot retrieval equipment and may typically include a microcatheter 8a and microwire 8b. Generally the microwire 8b is used to direct the microcatheter 8a safely beyond the site of the clot/thrombus in the brain vessel with the microwire subsequently being removed. Thereafter, the clot retrieval device 8c is introduced through the microcatheter to be deployed across the clot. As known to those skilled in the art, there may be variations in the actual clot retrieval device. For example, clot retrieval may be conducted by applying suction and pulling the clot into the microcatheter. Similarly these would be a different set of components if an acute myocardial infarction was being treated and would generally include microwires, angioplasty balloons and stents (not shown).

FIG. 9 shows miscellaneous equipment including various sizes syringes 9a, 9b, rotating hemostatic valves 9c, 3-way stop cocks 9d, gauze 9e and steri-strips 9f contained in a single module. The miscellaneous equipment is preferably part of a distinct module separable from the other modules.

Figure 10:
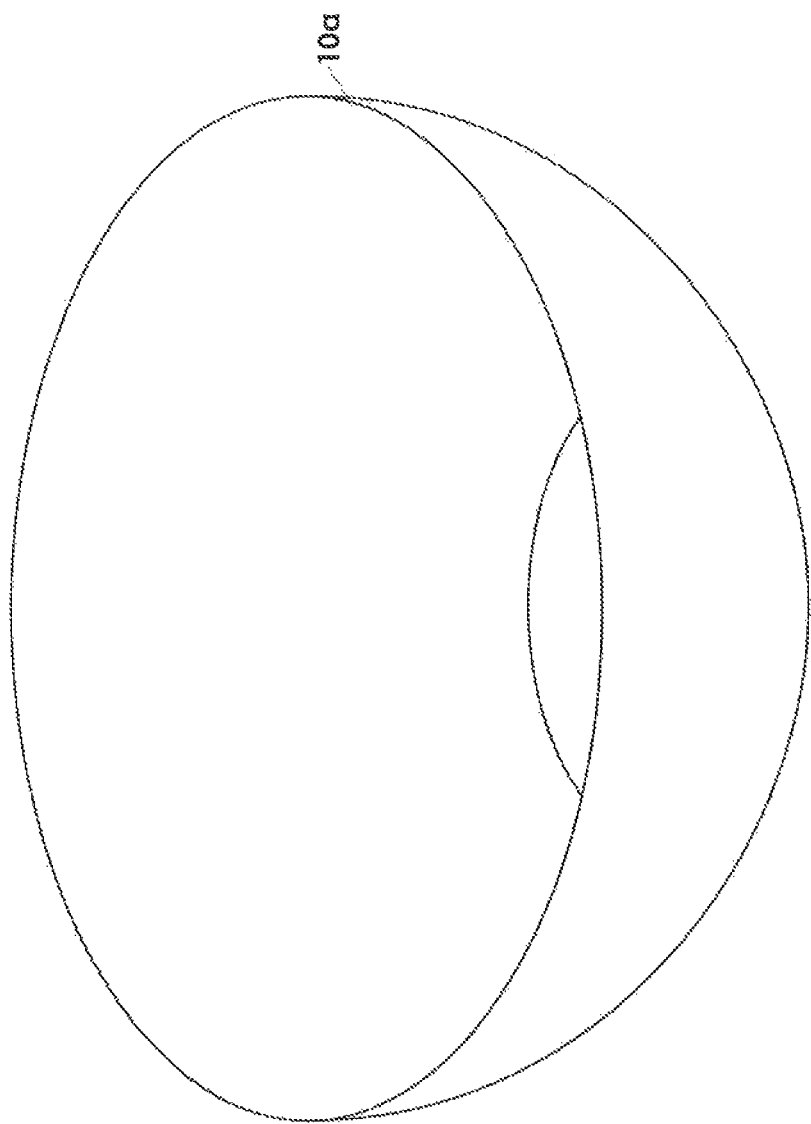
FIG. 10 is an isometric view of a typical bowl for inclusion in a module of a recanalization kit in accordance with one embodiment of the invention.

FIG. 10 shows a typical surgical bowl 10a. The bowls may include at least one large bowl used for keeping wires and catheters and at least one smaller bowl for holding contrast agent and/or saline. As shown in FIGS. 1, 1A, 1B, 1C and 1D, individual trays may contain one or more compartments 10a, 10b, 10c, 10d for bowls. Physical bowls may be separable from a tray or may be integrally formed within the tray. In one embodiment as shown in FIG. 1D, a large bowl 10a (i.e. a deeper bowl) may be formed as part of a "double height" tray 12a, whereas as smaller bowl 10b (e.g. for holding contrast agent) may be formed as "single height" tray 12c. Non-separable bowls may include a sterile seal 10e covering the bowl opening. The trays may also be used as supports for any separable bowl.

The foregoing FIGS. 2-10 show various generic equipment used in a typical IA recanalization procedure. However, it is understood that each module may include other generic and more specific equipment including but not limited to additional tubing, dilators, sheaths, stent retrievers, other wire, contrast filled syringes, sponges, diagnostic catheters, balloon guide catheter introducer, balloon guide catheter, Shuttle™ (Cook Medical), introducer (or similar) and Shuttle™ (or similar) (Cook Medical).

In addition, in one embodiment of the kit, allowances for different patient sizes is made. For example, it is preferred that more than one diagnostic catheter be included to allow for variance in the aortic arch anatomy of a patient. Similarly more than one microcatheter or microwire may be included to allow for variance in intracranial anatomy. Similarly more than one clot retrieval devices of varying sizes may be included to allow for variance in clot length. Also, given that clot retrieval devices are the most expensive part of the kit, in one embodiment, the different clot retrieval devices are individually sealed within the kit to allow for the collection and re-use of equipment that are not used for the procedure. For example, unused clot retrieval equipment can be returned to the manufacturer or supplier for re-packaging within a new kit. In this regard, the kit may also include an equipment return module in the form of pre-addressed courier labels and/or return packaging that enables the medical team to package unused equipment (particularly high value equipment) at the end of the procedure for return to the manufacturer or supplier. Upon receipt of unused equipment, the manufacturer will repackage such equipment for inclusion in another kit. As such, the hospital/facility returning equipment to the manufacturer can receive a credit against the original purchase price of the kit.

Figure 11:
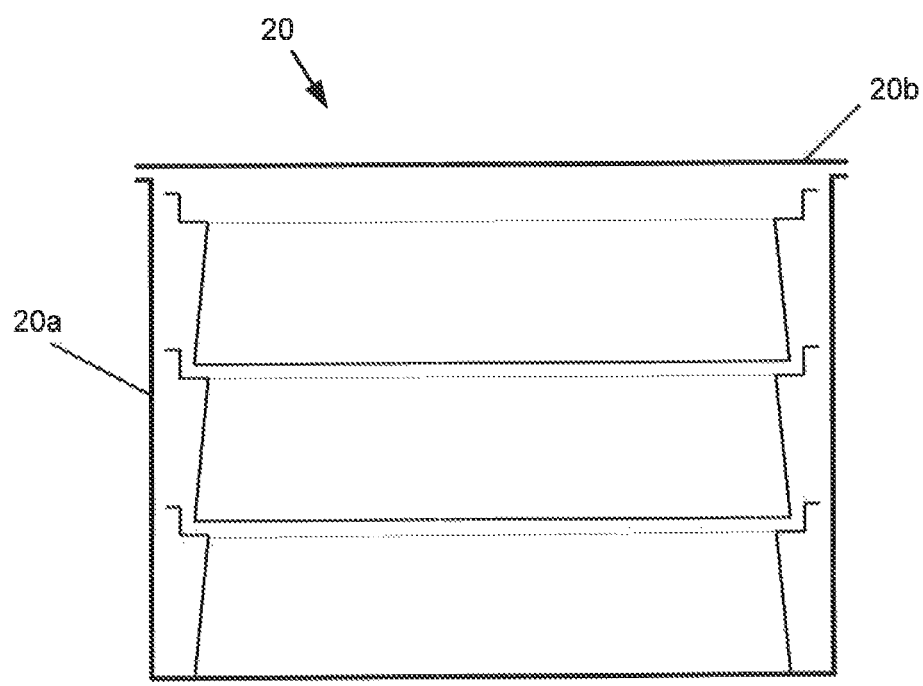
FIG. 11 is a conceptual and side schematic view of an intra-arterial (IA) recanalization kit with exterior packaging in accordance with one embodiment of the invention.

As shown in FIG. 11, in a three-tray stacked configuration, each of the three compartment layers may be contained in a larger sealable package 20 having a body 20a and removable lid 20b that provides and ensures sterility. In this embodiment, the kit is generally sized to fit on standard operating room tables such that the compartment layers can be removed from the larger package and moved to a desired location in the operating room or spread out on operating room table.

In operation, the kit 10 is available to medical teams in a treatment/operating room. The kit is placed on a table and the outer sealed package is opened to enable access to individual modules. Depending on the embodiment, individual modules may be separated to enable different team members to have close access to the specific equipment they require at different locations.

As shown in FIG. 12, each of the modules including a surgical site preparation module, tube and catheter preparation module, arterial vessel access module, procedure module, and optional miscellaneous equipment module, wound closure and equipment return module are shown in relation to a typical time sequence. That is, initially, the medical team will access the skin preparation equipment (FIG. 2) to shave and clean the IA access locations. Drapes (FIG. 3) are applied to the surgical sites.

Pressure bag preparation utilizing equipment within the tube and preparation module is initiated either simultaneously with surgical site preparation or shortly after. Pressure bag preparation generally includes the steps of inserting saline bags within pressure pumps to allow slow forward flow of saline through the groin sheath, guide catheter and microcatheter so as to prevent reflux of blood into these catheters.

After the patient is draped and the pressure bags prepared, the puncture equipment (FIG. 4) from the arterial access module is utilized to anesthetise the puncture area (preferably the groin) and effect the puncture for catheter insertion.

All catheters, wires, microcatheters, microwires and sheaths are flushed prior to use using equipment from the tube and catheter preparation module and procedure module. This may be done directly with a saline filled syringe or with the use of the manifold 6a.

Catheter preparation generally requires careful flushing of the catheters. As in a typical IA procedure, multiple catheters will need to be prepared, each of which, if flushed individually requires an additive amount of time to complete. Hence, in a preferred embodiment, the kit will include a multiflush system in the form of a manifold 6a (FIG. 6) enabling multiple catheters to be simultaneously flushed and thereby save time in the procedure.

The manifold 6a will generally include a first fluid conduit 6g enabling fluid from a flushing system (e.g. a saline filled syringe 9a) to be simultaneously flushed through each connected catheter. Importantly, as the flow resistance may be different for each catheter, the manifold will include openings and connectors (6b-6f) of varying sizes to enable each catheter to be individual connected and ensure that each catheter is adequately flushed. As well, a separate manifold system may also be included for the microcatheter, microwire, and clot retrieval devices etc. (FIG. 8, 8A) for those devices that are manufactured in a spiral tube and need to be flushed on the outside and the inside. As mentioned above, the manifold allows for these differences so that all of these spaces are adequately flushed at substantially the same rate.

Rotating hemostatic valves (RHVs) and three-way stop cocks may also be pre-attached to the catheters and microcatheters at appropriate places thereby obviating the need for separately flushing these and having to attach them. Importantly, by having the RHVs and stop cocks pre-attached can save significant time in the preparation of the catheters for the procedure which can reduce the time to complete the procedure. The RHVs and/or three-way stop-cocks may be adjusted to ensure that the flow resistance through each catheter is substantially the same so that the progression of flushing fluid through each catheter occurs at roughly the same rate. The openings (6b-6f) of a manifold will preferably be provided with removable caps (not shown) so that if all openings do not require a catheter to be attached, that opening will remain sealed.

As different physicians and teams may have different requirements depending on their specific practices, different kit configurations may be assembled from typical equipment. Typical equipment for IA procedures is listed in Appendix A.

A miscellaneous equipment module containing miscellaneous equipment, a wound closure module to enable wound closure at the end of the procedure and/or an equipment return module may also be included.

Furthermore, as noted above, as different patients have different anatomies, a "standard" kit may include additional sizes of components.

In another aspect of the invention, kits may be "custom" designed by medical teams. In this case, specific trays of equipment may be selected from an inventory of equipment, wherein the medical team/physician is able to assemble a specific package of equipment through online access to a website allowing physicians to design a specific kit from available inventories of equipment.

Importantly, kits can also provide physicians with the opportunity to travel between medical facilities to conduct procedures. That is, given the acuity of various medical situations and the level of specialization required to do certain procedures, physicians may take call for multiple hospitals where variations in equipment, staff and other parameters may be present and could present problems in the timely delivery or execution of a procedure. In such situations, physicians trained to conduct particular procedures could carry one or more kits and thus be able to efficiently conduct the procedure without necessarily having to know the layout and workings of different facilities. That is, by knowing that the kit contains all the necessary equipment, the physician will be able to carry out the procedure with less dependence on an 'unfamiliar' team. This may also obviate the need to move patients between hospitals by ambulance which is substantially more expensive and time consuming than having a physician move between hospitals.

Further still, the kit will enable procedures to be conducted in other areas within a facility in the event that equipment failure, natural disasters or other factors necessitate the need to conduct procedures outside a typical location.

Further still, the kit will allow for a greater degree of standardization across different teams within the same center, across varying levels of training and across various centers. This standardization is likely to result in further increase the efficiency of treatment for a number of procedures.

OTHER PROCEDURES

Importantly, as discussed above, the present invention may be utilized in other procedures in which different modules of equipment may be assembled.

In addition, it should be noted that revascularization techniques and recanalization techniques may be applied to both acute stroke and acute MI patients depending on the particular pathology of the patient.

SUMMARY

In summary, the present invention seeks to provide time savings to medical teams in acute situations and particularly to present medical equipment to personnel in the order that it is needed and to prevent the need to look for or assemble equipment. In addition, the invention seeks to reduce the time that may be required to prepare specific equipment for a procedure. In addition, use of the invention can improve training for specific procedures as well as improve standardization of procedures across different medical facilities which will lead to improved patient outcomes and lower the costs of delivering particular medical services.

While specific embodiments of the invention have been shown and described in detail to illustrate the application of the principles of the invention, it will be understood that the invention may be embodied otherwise without departing from such principles.

APPENDIX A

Representative List of Current Equipment Used in IA Recanalization Procedures
1. Cleaning solution—2
2. Large drape with holes—1
3. Large drape to cover feet end—1
4. Several small absorbent drapes
5. Puncture needle
6. Scalpel
7. Syringe along with or preloaded with topical anesthetic
8. Puncture wire
9. Sheath with dilator
10. 3 pressure bags
11. 3 pressure pumps
12. 3 connecting lines
13. Guiding catheter sheath (Shuttle™ or equivalent) with introducer
14. Balloon guide catheter with introducer
15. Diagnostic catheters to allow access beyond the aortic arch or coronary guide catheters
16. Many different syringes of different sizes (8)
17. Steri strips
18. Microcatheter (Rebar 18™ or equivalent)
19. Microwire
20. Clot Retrieval Device or angioplasty balloon or balloon mounted/self expanding stent
21. Rotating hemostatic valves—4
22. 3 way valves—4
23. Torque device—2
24. Arterial closure device: Angioseal™ or equivalent
25. Big bowl (to hold all the wires)
26. Small saline bowl
27. Contrast bowl
28. Discard bowl

What is claimed is:

1. A method of providing a modularized bundle of equipment for a recanalization procedure for decreasing preparation and surgical time for a recanalization procedure in the treatment of acute stroke, the method comprising the steps of:

incorporating at least one tray having a plurality of compartments containing a plurality of equipment modules including a surgical site preparation module containing sterilized surgical equipment for surgical site preparation, and an arterial access module for a recanalization procedure; and incorporating the compartments with outer packaging to provide a sterile seal to the equipment modules enabling members of a surgical team to initiate preparatory steps of the recanalization procedure without requiring assembly of a complete medical team, the surgical site preparation module having at least one compartment containing cleaning and draping equipment including at least one surgical drape for a distal arterial access site and cleaning solution, the arterial access module having at least one compartment containing equipment including at least one of a scalpel, a local anesthetic syringe, local anesthetic, a puncture needle, forceps and an introducer wire.

2. A method as in claim 1, further comprising the step of incorporating a tube and catheter flushing module within the modularized bundle.

3. A method as in claim 2, further comprising the step of incorporating a procedure equipment module including tube and catheter equipment to conduct a recanalization procedure within the modularized bundle.

4. A method as in claim 3, wherein the procedure equipment module includes intra-arterial recanalization equipment, the intra-arterial recanalization equipment including a plurality of catheters for accessing neck and brain vessels and clot retrieval.

5. A method as in claim 3, wherein each catheter within the procedure equipment module includes a pre-attached rotating hemostatic valve (RHVs) or three-way stop-cock.

6. A method as in claim 3, wherein the procedure equipment module includes at least two clot retrieval devices individually sealed within the procedure equipment module to enable collection and re-use of equipment unused in the procedure.

7. A method as in claim 6, further comprising providing an equipment return module having labeling and packaging for packaging unused equipment for return to a manufacturer.

8. A method as in claim 2, wherein the tube and catheter flushing module includes at least one catheter flushing manifold, the catheter flushing manifold including a first port for operative connection to a flushing system and at least two catheter openings for connection to catheters and wherein activation of the flushing system enables simultaneous flushing of each connected catheter.

9. A method as in claim 8, wherein the at least two catheter openings have different diameters.

10. A method as in claim 2, wherein each of the surgical site preparation module, tube and catheter flushing module and arterial access module are separate trays separable from one another.

11. A method as in claim 10, wherein the tube and catheter flushing module includes catheter flushing equipment.

12. A method as in claim 2, wherein surgical equipment in each of the surgical site preparation module, the tube and catheter flushing module and the arterial access module include module packaging only and are not individually packaged.

13. A method as in claim 1, wherein the at least one tray includes a lower tray stackable with an upper tray and the upper tray includes the surgical site preparation module.

14. A method as in claim 1, wherein the at least one tray includes a lower tray stackable with an upper tray and wherein the lower tray includes the surgical site preparation module.

15. A method as in claim 1, wherein the at least one tray is a single tray.

16. A method as in claim 1, wherein the at least one tray includes a combination of stacked and unstacked trays.

17. A method as in claim 1, wherein the at least one tray includes a bowl compartment integrally formed with the at least one tray.

18. A method as in claim 17, wherein the bowl compartment supports a separable bowl.

19. A method as in claim 18, wherein the bowl compartment includes a sterile seal on an upper surface of the at least one tray and the bowl compartment supports liquid within the tray.

20. A method of providing a modularized bundle of equipment for a recanalization procedure for decreasing preparation and surgical time for a recanalization procedure in the treatment of acute stroke, the method comprising the steps of:

providing at least one tray having a plurality of compartments containing a plurality of equipment modules comprising sterilized surgical equipment for surgical site preparation, and arterial access for a recanalization procedure and providing the compartments with outer packaging to provide a sterile seal to the equipment modules enabling members of a surgical team to initiate preparatory steps of the recanalization procedure without requiring assembly of a complete medical team, wherein the plurality of equipment modules comprise a surgical site preparation module having at least one compartment containing cleaning and draping equipment including at least one surgical drape for a distal arterial access site and cleaning solution, the plurality of equipment modules further comprising an arterial access module having at least one compartment containing equipment including at least one of a scalpel, a local anesthetic syringe, local anesthetic, a puncture needle, forceps and an introducer wire.

* * * * *